United States Patent [19]

Siclari

[11] 4,192,813

[45] Mar. 11, 1980

[54] OMEGA-HYDROXY ALKENOIC ACID

[75] Inventor: Francesco Siclari, Barlassina Milan, Italy

[73] Assignee: Snia Viscoas Societa Nazionale Industria Applicazioni Viscosa S.p.A., Italy

[21] Appl. No.: 885,537

[22] Filed: Mar. 13, 1978

Related U.S. Application Data

[62] Division of Ser. No. 486,992, Jul. 10, 1974, Pat. No. 4,085,127.

[30] Foreign Application Priority Data

Jul. 11, 1973 [IT] Italy .............................. 26479 A/73

[51] Int. Cl.² ........................... C11C 3/02; C11C 1/00
[52] U.S. Cl. .............................. 260/410.9 R; 260/413
[58] Field of Search ............ 260/413 R, 413 K, 413 L, 260/413 Q, 410.9 R, 410.9 M, 410.9 Q

[56] References Cited

U.S. PATENT DOCUMENTS

| | | | |
|---|---|---|---|
| 3,856,833 | 12/1974 | Siclari et al. | 260/413 |
| 3,868,392 | 2/1975 | Siclari et al. | 260/340.3 |

OTHER PUBLICATIONS

Kotick et al., Chem. Abst., vol. 70, No. 29237p (1969).

*Primary Examiner*—John F. Niebling
*Attorney, Agent, or Firm*—Shelsinger, Fitzsimmons, Shlesinger

[57] ABSTRACT

An omega-hydroxy alkenoic acid containing 8 or 12 carbon atoms is obtained by the selective reduction of the carbonyl group of an omega-formyl alkenoic acid, for example by the use of sodium borohydride, and wherein the starting acid is produced by the ozonization and transposition of a polyunsaturated hydrocarbon cycloolefin.

2 Claims, 6 Drawing Figures

OHC-CH$_2$-CH$_2$-CH=CH-CH$_2$-CH$_2$-COOH     T.Q. (NaCl)

OMEGA-HYDROXY ALKENOIC ACID

This application is a division of our copending U.S. application Ser. No. 486,992, filed July 10, 1974 now U.S. Pat. No. 4,085,127.

This invention relates to omega-hydroxy alkenoic acids and a method for their production. The hydroxy acids of the present invention may be made from omega-formyl alkenoic acids whose production by partial ozonolysis of polyunsaturated cycloolefins is described and claimed in our above-noted U.S. patent application, the contents of which may be referred to if necessary for the purpose of better understanding the hereinafter described invention. Thus it is preferred to prepare the hydroxy acids of the present invention starting from cycloolefins, which are readily available.

The unsaturated omega-hydroxy acids have important applications, e.g. use in making polymers or copolymers whose reactivity, due to the presence of double bonds, enables them to be used for the manufacture of products which in turn possess desirable properties. Examples of such products are textile products possessing a high degree of dye-ability and additives for antistatic agents or for resins, all of which is easily understandable by persons skilled in the art.

The present invention provides an ethylenically unsaturated omega hydroxy alpha carboxylic acid wherein the or each ethylenic unsaturation is separated from both the terminal —CH$_2$OH group and the terminal carboxylic acid group by an even number of saturated carbon atoms. Preferred compounds of the invention contain 8 or 12 carbon atoms e.g. 8-hydroxy-cis-4-octenoic acid and 12-hydroxy dodeca-t-t-4,8-dienoic acid. The omega-formyl alkenoic acids used as starting materials for the preparation of the omega-hydroxy alkenoic acids are preferably obtained by reacting a polyunsaturated cycloolefin with ozone to form a monoozonide, the reaction being carried out in a solvent system comprising a non-polar solvent and a polar solvent, comprising at least one carboxylic acid and at least one anhydride of a carboxylic acid, the concentration of the cycloolefin in the reaction mixture being kept between 10 and 40% by weight, to form a solution of the mono-ozonide in the polar solvent, which solution is a separable phase, and subjecting the mono-ozonide to transposition in the presence of a catalyst comprising a carboxylic acid anhydride in admixture with an alkali metal salt or organic base salt of a carboxylic acid or an alkali metal alcoholate, which method is described and claimed in our above-noted copending application.

As is known, cyclododecatriene-1,5,9 and likewise cyclodecadiene and cyclooctadiene, are products that are obtained by known processes of cyclization of butadiene, are currently available on the market and are supplied by refineries and industries which treat and process petroliferous products. These cycloolefins are in general transformed by the petroleum processing industries themselves, or by the utilizer industry, into the corresponding cyclomonounsaturated product. For example, cyclododecene is obtained, which is for example utilized for the production of conventional nylon 12.

The industrial utilization of starting materials which contain more than one unsaturation, to obtain, with high conversions, first acidic aldehydes and then omega-hydroxy alkenoic acids and their derivatives is not known in the technical and patent literature of the art. Thus, at least within the limits of the applicants' knowledge, it can be held that no such technology existed previous to the present invention.

The principal but not the only compounds of the invention are unsaturated linear omega-hydroxy acids, usually containing from 8 to 12 carbon atoms. When obtained from 11-formyl 4,8-undecadienoic acid they correspond to the formula:

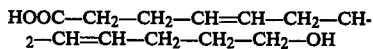

HOOC—CH$_2$—CH$_2$—CH=CH—CH$_2$—CH$_2$—CH=CH—CH$_2$—CH$_2$—CH$_2$—OH

Clearly, the compounds that are obtained from other omega formyl alkenoic acids having 8 or 10 carbon atoms correspond to similar formulae, but the residual acid indicated has 8 and 10 carbon atoms respectively.

The omega-formyl alkenoic acids for use in the present invention may be prepared from the starting polyunsaturated cycloolefins, e.g., cyclododecatriene, cyclodecadiene or cyclooctadiene (independently, as has been said, of the form or mixture of isomeric form sand also, in the specific case of cyclododecatriene, possibly in admixture with cyclododecadiene) by means of a sequence of steps and operations during which not more than one unsaturation is removed, the said sequence comprising a selective ozonization from which is obtained the mono-ozonide which is then converted by transposition into the omega-formyl-alkenoic acid, in the case in point 11-formyl-4,8-undecadienoic acid, 9-formyl-6-nonenoic acid, 9-formyl-4-nonenoic acid and 7-formyl-4-heptenoic acid.

In the course of the detailed description that follows, referred to various examples of execution of the invention, certain omega-hydroxy alkenoic acids and their possible uses are described.

From among the unsaturated products that can be obtained according to the invention, the industrial importance of which is both foreseen and easily imaginable, there can be mentioned 12-hydroxy-4,8-dodecadienoic acid and 8-hydroxy-4-octenoic acid, from which there can be obtained unsaturated esters and/or polyesters, e.g. the methyl ester of the above-indicated acids.

To further describe the present invention, there is hereafter set out a detail exemplification of methods of obtaining the novel products according to the invention. This disclosure is completed by the annexed drawings, in which:

FIG. 3 shows the IR spectrum of 11-formyl-t,t-4,8-undecadienoic acid;

FIG. 4 shows the IR spectrum of the 12-hydroxy-t,t-4,8-dodecadienoic acid obtainable from the unsaturated acidic aldehyde of FIG. 3;

FIG. 5 shows the IR spectrum of the methyl ester of the hydroxyacid of FIG. 4;

FIG. 6 shows the IR spectrum of 7-formyl-cis-4-heptenoic acid.

Figure 3:
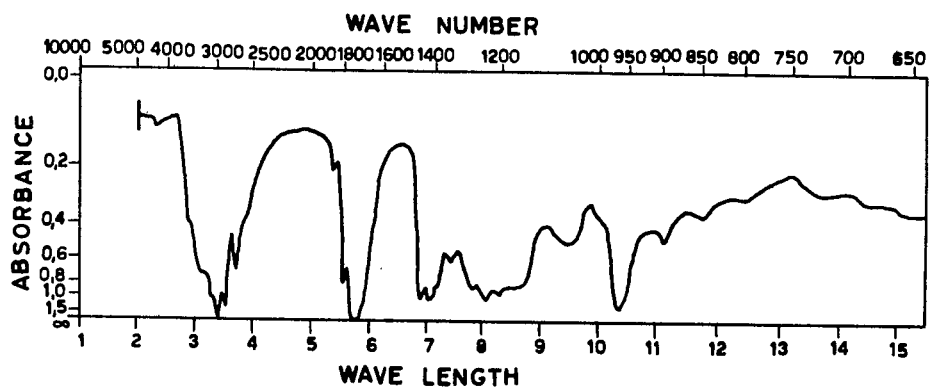
FIGS. 3 and 4 to 6 show a number of IR and NMR spectra in respect to certain unsaturated compounds obtainable according to the invention, in particular.
Figure 4:
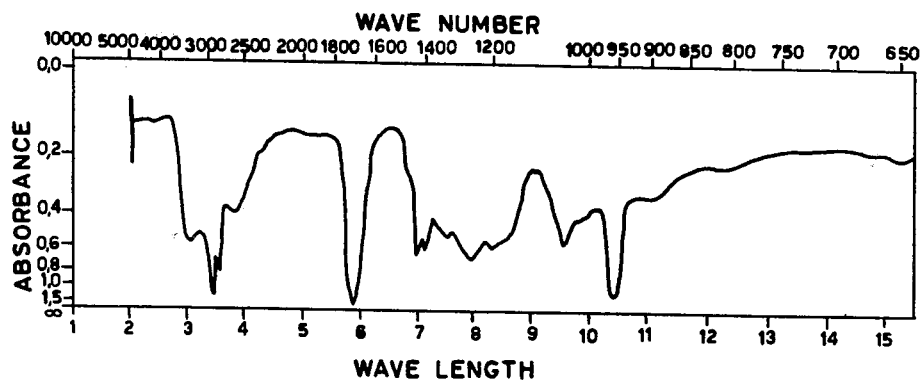
Figure 5:
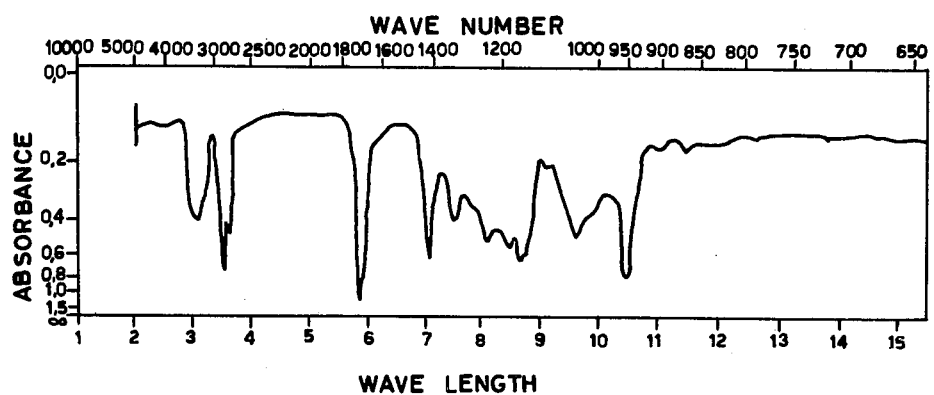

Examination of these spectra clearly reveals the following: for the group represented by FIG. 3 to FIG. 5 the band of the trans double bond (960 cm$^{-1}$) is preserved. In the 12-unsaturated hydroxyacid derivatives of FIG. 4 and methyl ester of FIG. 5 the band of the OH appears at approximately 3200 cm$^{-1}$.

Figure 6:
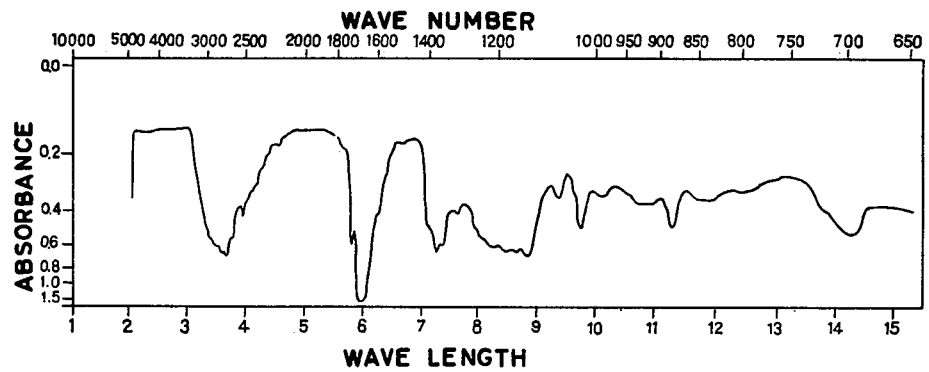

FIG. 6 represents the 8-unsaturated acidic aldehyde obtained from the cis. cis-1,5-cyclooctadiene, the cis band between 680 and 740 cm$^{-1}$ is preserved, while there are clearly visible the bands characteristic of the aldehyde group.

In the ensuing description specific indication will be given of the sterioisometric forms and their proportions in the mixtures utilized, in the interests of greater bearing on the industrial field, in view of the availability on the market of polyunsaturated cycloolefins, e.g. cyclododectariene, cyclodecadiene and cyclooctadiene, in various stereoisomeric forms.

In the IR spectra shown in FIGS. 4 to 5, on the other hand, 11-formyl-t,t-4,8-undecadienoic acid has been specified as starting material simply because the derivatives show clearly in the IR the trans isomerism of the double bond, without this in any way limiting the scope of the invention. The preparation of the starting omega-formyl alkenoic acids may be carried out for instance according to the method and in the apparatus schematically represented in FIG. 1.

The initial step of treatment of the polyunsaturated cycloolefin with ozone is carried out in the vessel or reaction environment indicated generally by 10, in association with an apparatus 12 for production of ozone, after prior preparation of a stationary phase consisting of a mixture of high-boiling saturated hydrocarbon, preferably obtained from mineral oil (Vaseline (Vaseline is a Registered Trade Mark) oil or refinery cuttings) with a polar solvent such as acetic acid, and/or acetic anhydride. The ozone is used in the form of a mixture of $O_2+O_3$ containing from 5 to 80 grams, and preferably from 15 to 60 grams of $O_3$ per cubic meter, or a mixture of $O_2+O_3+CO_2$ containing from 5 to 50 grams of ozone per cubic meter. Alternatively the ozone may be mixed with purified air stripped of nitrogen oxides by passing through sodium acetate dissolved in acetic acid or by passing over CuO. The mixture may contain from 1 to 50 grams of $O_3$ per cubic meter. The ozonide is continually deposited in the container bottom as it is formed as a heavy phase P formed by solution in the acetic acid and/or acetic anhydride. This stage may be carried out at any temperature between 5° C. and 45° C. The acetic acid and/or acetic anhydride is fed into the apparatus at 14 and also recycled at 16. Cyclododecatriene is fed into the vessel 10 continuously at 18, while at 20 the oxygen or other gas used as a vehicle for ozone is discharged.

The heavy phase 22 is metered and sent at 24 into a transposition apparatus 26 into which there is also metered at 28 an additional transposition catalyst, preferably sodium acetate, and possibly potassium acetate, sodium propionate or potassium propionate.

The transposition stage which is the decomposition of the ozonide in the vessel 26 may be carried out at a temperature of from 10° to 50° C., a solution of the unsaturated acidic aldehyde in acetic acid and/or acetic anhydride being obtained. Preferably, the transposition run is carried out progressively in a set of vessels and in the embodiment of FIG. 1 this is achieved by transferring the solution to a second apparatus 30 from which the product is passed to an evaporator 32. From the evaporator the excess acetic acid is removed at 34 and the remaining acetic acid and/or acetic anhydride which is distilled off is recycled at 16 into the ozonization vessel or environment 10. The temperature in the two transposition stages (26-30) can either be the same or it can be different. Usually it is higher in vessel 30.

The anhydride of the acidic aldehyde left in the evaporator 32 is transferred to a hydrolysis apparatus 34a. The hydrolysis of the acidic aldehyde anhydride is carried out in this apparatus. Hydrolysis may be effected with water at a temperature of from 50° C. to 100° C. The solution is transferred to an evaporator 36, wherefrom the hydrolysis water is recycled at 38 into the hydrolysis apparatus 34a. A mixture of the excess water and possibly acetic acid is dumped, at 40. The acidic aldehyde is discharged from the bottom of the evaporator 36.

An omega-formyl alkenoic acid obtained preferably as above mentioned, is selectively reduced to give the omega-hydroxy alkenoic acids of the present invention, e.g. by sodium borohydride. The omega-formyl alkenoic acid can be treated with a mixture of ethanol and aqueous sodium bicarbonate to neutralize the acid and then with an aqueous solution of sodium borohydride, suitably at 0° C. for initial period followed by a longer period at room temperature.

The omega-hydroxy alkenoic acids may be polymerized or may be esterified.

The corresponding unsaturated alpha-omega diol may be formed as a by-product during the preparation as described above of an omega-hydroxy alkenoic acid. Such diols may be reduced to the corresponding saturated alpha, omega diols.

Figure 1:
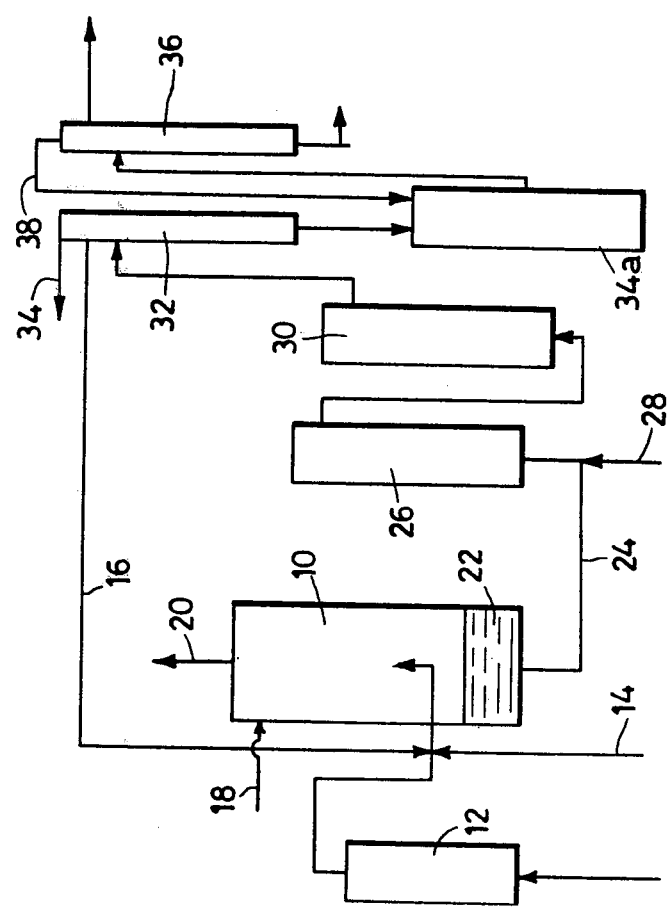
FIG. 1 shows schematically, in that the various components are individually well known, an installation utilizable for the preparation of 12-formyl dodecadienoic acid from cyclododecatriene, for use in the present invention.
Figure 2:
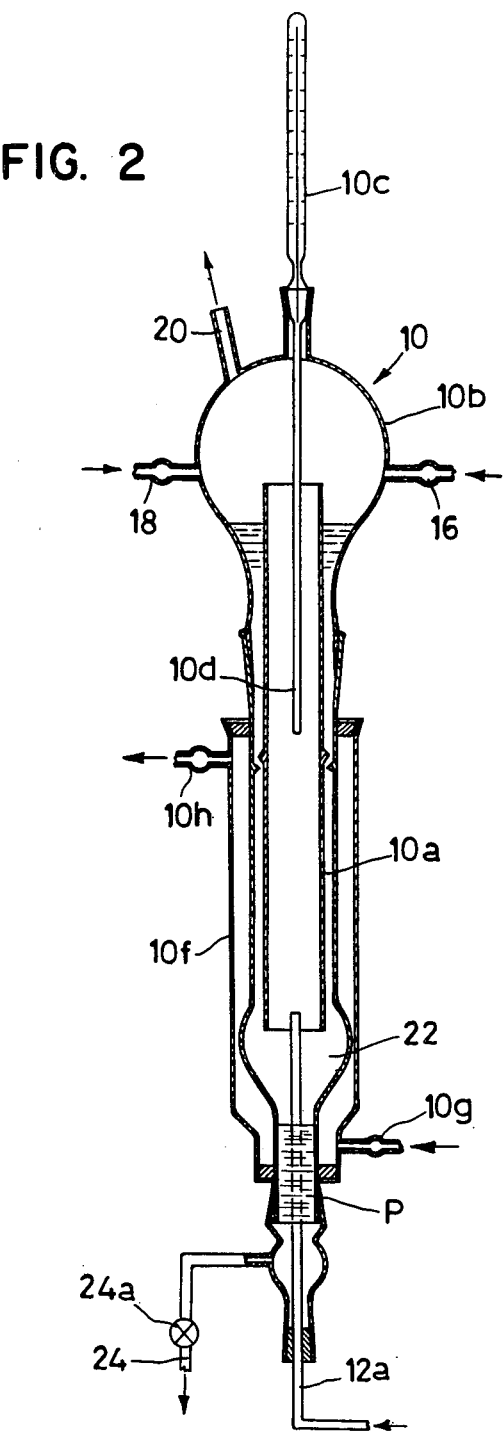
FIG. 2 shows in greater detail the equipment preferably used for the ozonization step.

A preferred embodiment of the ozonization apparatus 10 is reproduced in detail, in FIG. 2 in which the same reference numerals connote the same parts as equivalent numbers in FIG. 1.

This apparatus comprises an internal reaction tube 10a, whose top end enters a flask 10b in which open the outlet 20 for the oxygen, and the ducts 18 for feeding in cyclododecatriene and 16 for feeding in the recycled acetic acid and/or anhydride. At 12a there is indicated the duct at the base of the reaction environment through which the product of the ozone ($O_2+O_3$) producing apparatus and at 24 there is indicated the discharge duct for the ozonide, equipped with a suitable valve 24a.

The apparatus is completed by an appropriate thermometer 10c whose sensitive bulb 10d is extended into the reaction tube. The portion in which reaction mainly occurs proper is cooled by a jacket formed by an outer jacket 10f for an appropriate coolant mixture, and having integral inlet and outlet fittings 10g and 10h.

There follow specific Examples describing parameters and conditions which are deemed more suitable for carrying out the invention, with high yields.

EXAMPLES-GROUP I (OZONIZATION)

I. (1) Ozonization of t,t,t-1,5,9-cyclododecatriene (CDT) in Acetic Acid-Acetic Anhydride-Paraffin Oil In this example there is described the preparation of the CDT mono-ozonide by ozonization in a mixed solvent, formed by acetic acid, acetic anhydride, and paraffin oil.

The CDT mono-ozonide can be employed to obtain unsaturated aldehyde acids, saturated and unsaturated dicarboxylic acids or polyaldehydes, which are useful products in themselves or for subsequent conversions.

In the vessel 10 of FIG. 1 there was charged 800 grams of t,t,t-1,5,9-cyclododecatriene (m.p.=30°-32° C.), purity 97.5%), 297 grams acetic acid, 503 grams acetic anhydride (purity 95.2%) and 6400 grams of paraffin oil. The temperature of the mixture was brought to 20° C. and of 113.5 grams/hour of ozone in 1700 liters/hour of oxygen (at ambient pressures) 736 grams/hour of acetic anhydride, 585 grams/hour of acetic acid, 400 grams/hour of CDT and 80 grams/hour of paraffin oil were continuously fed into the vessel.

A heavy phase was continuously deposited on the bottom of the reactor vessel at the rate of 1900 grams/hour, which phase consisted of CDT mono-ozonide dissolved in the acetic anhydride-acetic acid mixture.

After 16 working hours, 30410 grams of ozonide solution had been continuously discharged from the bottom of the reactor and sent to the transposition apparatus (No. 26, FIG. 1). The content of active oxygen (from iodometric assay according to Lohaus) was 37 mols overall, corresponding to 7760 grams of CDT ozonide as expressed in its classical form, the remainder being acetic anhydride, acetic acid and small quantities of cyclododecatriene and paraffin oil.

The total reacted cyclododecatriene (calculated from the amount charged, from what is left in the reactor and what is contained in the heavy phase) was 37.5 mols, a result which, as a rough estimate, indicates that CDT has reacted with ozone in a ratio of 1:1.

These data show that it is possible quantitatively to convert a polyunsaturated cycloolefin into its mono-ozonide. By employing paraffin oil, hydrocarbon losses in the reaction gas are prevented.

I (2) Ozonization of cis,cis-1,5-cyclooctadiene

The Example I is repeated, using cyclooctadiene (COD) as polyunsaturated cycloolefin.

From the relative quantities of cycloolefin and ozone reacted it was seen that, in this case, also, the ozone reacted in 1:1 molar ratio with the COD. The ozonide of the COD is a product useful for obtaining unsaturated aldehyde acid, bicarboxylic acids, etc.

EXAMPLES-GROUP II (TRANSPOSITION)

The transposition of the CDT monoozonide into 11-formyl-t,t-4,8-undecadienoic acid may be carried out catalytically as described in the Examples that follow.

II (1) Transposition of the Mono-Ozonide of t,t,t-CDT into 11-Formyl-t,t-4,8-Undecadienoic Acid The ozonide solution (1900 grams/hour) coming from the apparatus 10 of FIG. 1, was sent continuously onto the bottom of a first transposition apparatus (26, FIG. 1) consisting of a 6-compartment steel cylinder fitted with thermometer, turbine type stirrer and temperature-regulation jacket kept at 20° C. The transposition apparatus was also continuously fed with 4.75 grams/hour of sodium acetate dissolved in 42.8 grams of acetic acid. The mixture issuing from the top of the first transposition apparatus passed to a second transposition apparatus (30, FIG. 1) which was the same as the first and was temperature-regulated at 30° C. Both the transposition apparatuses were kept under an inert gas atmosphere (carbon dioxide). The overall stay time was 7 hours and 30 minutes. Stirring was very slow.

Taking as equal to 100 the percentage of active oxygen (peroxidic oxygen) at the inlet of the first transposition apparatus, the analysis of this latter variable at the outlet of the first transposition apparatus was 31.7% and at the outlet of the second transposition apparatus was 7.6% (conversion 92.4%). The solution coming out of the second transposition apparatus was sent to a liquid-film evaporator (32, FIG. 1) to remove the solvents. The residue, 526 grams/hour, of a liquid oily at room temperature, was continuously treated at 72° C. with 526 grams/hour of water (stay time 60 minutes) in an inert gas (nitrogen) atmosphere (34, FIG. 1). The water was again evaporated as a liquid film (36, FIG. 1). 539 grams/hour of an oil residue were obtained which still contained small amounts of water, acetic acid and paraffin oil; the residue has the following characteristics:

| Aldehydric groups | 4.2 millimols/gram |
| Acidic groups | 4.5 millimols/gram |
| double bonds | 8.8 millimols/gram |

The product boiled at 180°-183° C. at 3 mm of residual pressure, and consisted of 11-formyl-t,t-4,8-undecadienoic acid.

II (2) Transposition of the Ozonide of Cyclooctadiene

The Example No. II (1) is repeated, using the product obtained in the Example I (3) and that is to say the monoozonide of cyclooctadiene (COD) was subjected to transposition.

There was obtained 7-formyl-4-heptenoic acid, which on analysis showed the following characteristics: b.p. at 2.3 mm. Hg=146.5° C. r/$D^{20}$=1.4744 double bonds (mmols from $H_2/g$.

|  | calculated | found |
|---|---|---|
|  | 6.4 | 6.5 |
| —CHO—groups (titration with $H_2NOH . HCl$) | 6.4 | 6.3 |
| —COOH groups (titration with NaOH) | 6.4 | 6.6 |

EXAMPLES-GROUP III (UNSATURATED DERIVATIVES OF THE ACIDIC ALDEHYDE)

III (1) Preparation of the 12-Hydroxy-dodecan-t,t-4,8-Dienoic Acid 50 grams of the unsaturated acidic aldehyde prepared for instance as disclosed in Example II (1) (b.p. at 3 mm Hg=180°-183° C.) were charged into a 1-liter glass flask and then, under stirring, 250 cc of ethyl alcohol were added; the mixture was cooled 0° C. and 19.2 grams of sodium bicarbonate dissolved in 250 ml of water were added. On completion of the addition of the sodium bicarbonate solution, the apparatus was placed under vacuum and the temperature was adjusted 20°-25° C.

When all the carbon dioxide had evolved, cooling was again effected to 0° C. and slow addition was made of 7 grams of sodium borohydride dissolved in 60 ml water. The solution was allowed to stand for 1 hour at 0° C. and overnight at room temperature then evaporation was carried out to small volume under vacuum in a stream of $CO_2$ in order to decompose most of the excess of sodium borohydride.

Then 50 ml of N/1 NaOH were added and the reaction mixture was extracted with ether; the ether extract was evaporated to dryness. In this way there was obtained a residue (2.2 grams) consisting of a mixture of cyclododecatriene and dodecadien (4,8)-diol-(1,12).

The aqueous phase, acidified with hydrochloric acid pH 2, was again extracted with ether and the extract was washed with 30 ml water, dried over magnesium sulfate and evaporated to dryness. The residue consisted of 39.5 grams of 12-hydroxydodecane-t,t-4,8-dienoic acid, as results from the following analytical data:

|  | Calculated millimols/gram | Found millimols/gram |
| --- | --- | --- |
| Hydroxyl group | 4.72 | 4.60 |
| Acidic groups | 4.72 | 4.68 |
| Double bonds | 9.44 | 9.20 |

III (2) Preparation of 8-Hydroxy-Cis-4-Octenoic Acid

Operation was carried out as described in the Example III (1) using the 7-formyl-cis-4-heptenoic acid, obtaining after reduction with $NaBH_4$ the 8-hydroxy-cis-4-octenoic acid.

III (3) Preparation of the Methyl Ester of the 12-Hydroxydodecane-t,t-4,8-Dienoic Acid 20 Grams of hydroxy acid obtained in the Examples III (1) were dissolved in ether and treated with an ethereal solution of diazomethane. By evaporation of the solvent there was obtained 21.5 grams of the methyl ester of the 12-hydroxydodecane-t,t-4,8-dienoic acid.

III (4) Preparation of 1,2-Dodecanediol

Dodecandien-(4,8)-diol-(1,12) (2 grams) was subjected to reduction in ethanol, using Pd on carbon as catalyst.

There was obtained, after filtration of the catalyst and evaporation of the solvent, 2.04 grams of 1,12-dodecanediol.

Having thus described our invention, what we claim is:

1. Omega hydroxy alkenoic acids containing 8 and 12 carbon atoms, respectively, and selected from the group consisting of 12-hydroxy-dodecane-t,t-4,8-dienoic acid, 8-hydroxy-cis-4-octenoic acid and esters thereof.

2. An ester as defined in claim 1, comprising the methyl ester of said 12-hydroxy-dodecane-t,t-4,8-dienoic acid.

* * * * *